United States Patent [19]

Bakshi et al.

[11] Patent Number: 5,248,836

[45] Date of Patent: Sep. 28, 1993

[54] PROCESS FOR THE PREPARATION OF ETBE

[75] Inventors: Amarjit Bakshi, The Hague, Netherlands; Edward M. Jones, Jr., Friendswood; Bobby A. Strain, Missouri City, both of Tex.

[73] Assignee: Chemical Research & Licensing Company, Pasadena, Tex.

[21] Appl. No.: 962,296

[22] Filed: Oct. 16, 1992

[51] Int. Cl.$^5$ ............................................. C07C 41/06
[52] U.S. Cl. ..................................................... 568/697
[58] Field of Search ........................................ 568/697

[56] References Cited

U.S. PATENT DOCUMENTS

| | | | |
|---|---|---|---|
| 4,232,177 | 11/1980 | Smith, Jr. | 585/324 |
| 4,307,254 | 12/1981 | Smith, Jr. | 568/697 |
| 4,336,407 | 6/1982 | Smith, Jr. | 568/697 |
| 4,950,803 | 8/1990 | Smith, Jr. et al. | 568/697 |

*Primary Examiner*—Howard T. Mars
*Attorney, Agent, or Firm*—Kenneth H. Johnson

[57] ABSTRACT

A process is provided for selective etherification of $iC_4=$ with EtOH to form ETBE in a distillation column reactor containing a fixed bed acid cation exchange resin as a catalytic distillation structure in a reaction distillation zone combined with a straight pass fixed bed reactor. A $C_4$ feed containing isobutene is mixed with the total liquid downflow from the catalytic distillation reactor and passed to a straight pass fixed bed reactor, where up to about 85% of the isobutene is reacted with ethanol in the distillation column reactor effluent. This stream is returned to the distillation column reactor at a point below where the liquid downflow is withdrawn and then fractionated on conventional trays to remove ETBE as a bottom product. The remainder of the feed from the straight pass fixed bed reactor is vaporized into the reaction distillation zone of the distillation column reactor, where the unreacted isobutene is reacted with down coming ethanol fed at the upper end of the reaction distillation zone. Any water in the ethanol feed is stripped out and carried out the distillation column reactor with the unreacted $C_4$'s.

16 Claims, 2 Drawing Sheets

PROCESS FOR THE PREPARATION OF ETBE

BACKGROUND OF THE INVENTION

1. Field of the Invention

The present invention relates to the production of ethyl tertiary butyl ether (ETBE) from the reaction of isobutene ($iC_4^=$) with ethanol (EtOH). More particularly the invention relates to a process using a primary straight pass reactor in combination with a catalytic distillation column reactor.

Related Art

The production of MTBE from the acid catalyzed reaction of $iC_4^=$ and MeOH is well known in the art. Generally the $iC_4^=$ is contained in a mixed hydrocarbon stream containing predominantly $C_4$'s which includes normal butenes, butanes and possibly lighter $C_3$ hydrocarbons. The $iC_4^=$ content of these streams is typically from 10-70 mole %. The MeOH preferentially reacts with the $iC_4^=$ to form MTBE with the remainder of the materials in the mixed hydrocarbon passing through essentially as inerts. The use of catalytic distillation particular method is exemplified by U.S. Pat. Nos. 4,232,177; 4,307,254; and 4,336,407 and the combination of the straight pass reactor and the distillation column reactor is disclosed in U.S. Pat. No. 4,950,803.

These ethers are produced in vast quantities throughout the world and employed as combustion and octane improvers in gasoline. Methanol is very easily used in the combined reactor system described in U.S. Pat. No. 4,950,803, which is the system of choice by most new facilities. Until recently methanol has been used in the commercial units; however, the high demand for the ethers has reduced the amount of methanol available and increasing the cost. There are recognized problems with the use of methanol in refinery systems for gasoline components, since the methanol must be essentially excluded from the gasoline, because of its tendency to phase out.

Ethanol, although it has some undesirable properties in gasoline, is now approved as a gasoline component and does not phase out as readily as methanol. Much ethanol that is available and will be available is made by fermentation of grains, and must be separated from the aqueous fermentation broth, normally by distillation. Unfortunately, water and ethanol form an azeotrope containing about 4 or 5 weight percent water, so that it is necessary to break this azeotrope using a two column system, in which the water is removed by a third component such as cyclohexane. The capital and operating cost of the azeotrope breaking systems adds to the cost of producing ethanol, which is an already expensive component for gasoline use. It would be better for ether production to use 95% "wet" ethanol; however, in all of the MTBE and ETBE syntheses, using the acid resin catalyst the presence of water can result in the production of tertiary butyl alcohol while also reducing the activity of the catalyst.

In the MTBE reaction using the combined reactors the isobutene containing feed and the methanol are fed as a mixed stream to the straight pass reactor, where about 85-90% of the isobutene is reacted, and the reaction product from the straight pass reactor is fed below the catalyst bed in the distillation column reactor, where the major portion of the unreacted isobutene is reacted to give total yield of 97+%. When this system is used for ETBE production the ethanol forms minimum-boiling azeotropes with the $C_4$ hydrocarbons at a concentration of about 2 weight percent at the operating conditions for the etherification. The $C_4$ distillate from the distillation column reactor contains the excess ethanol, but in many cases the ethanol carried into the catalytic distillation structures is not sufficient to react with the unreacted isobutene from the straight pass reactor. One solution is to feed more ethanol directly to the catalyst bed in the column; however, because of the limited amount of ethanol which could be removed by reaction in the column, and the limited amount which could be removed overhead as the $C_4$-ethanol azeotrope, this scheme is likely to produce an excess of ethanol which must be removed with the bottom product ETBE, and would therefore be an undesirable impurity in the product.

The present invention provides a process and apparatus for the selective etherification of isobutene and overcomes the ethanol deficiency in the distillation reactor bed while providing additional temperature control in the straight pass reactor. A particular advantage of the present invention is that it allows the use of the 95% ethanol as a feed.

SUMMARY OF THE INVENTION

The present invention is a process for the selective etherification of $iC_4^=$ in $C_4$ streams with ethanol to form ETBE and the apparatus comprising a combined straight pass reactor/distillation column reactor system for carrying out the process. Preferably both reactors contain a fixed bed acid cation exchange resin with the bed in the distillation column reactor prepared as catalytic distillation structures in a reaction distillation zone. Briefly the apparatus is a system comprising a straight pass reactor having an inlet and a $C_4$ feed line, an outlet and a product line connecting said outlet to a distillation column reactor at a point below a catalyst bed prepared as a catalytic distillation structure, an ethanol feed line to said distillation column reactor above said catalyst bed, a tray positioned below said catalyst bed and above said product line for collecting the total liquid downflow in said column and a line connecting said tray to the inlet of said straight pass reactor.

The preferred process of the present invention comprises feeding an isobutene containing $C_4$ stream and a stream containing ethanol and ethyl tertiary butyl ether to a straight pass reactor containing a fixed bed acid cation resin catalyst and selectively reacting ethanol and a portion of said isobutene to form a first product stream; sending the total first product stream comprising ethanol, isobutene and ethyl tertiary butyl ether from said straight pass reactor to a catalytic distillation column reactor at a point below an acid cation exchange resin prepared as catalytic distillation structure, which is defined as the reaction distillation zone, and fractionating said first product stream to remove ethyl tertiary butyl ether as a bottoms product from said column and vaporizing said ethanol and isobutene into said reaction distillation zone, feeding ethanol to said column at a point above said acid reaction distillation zone wherein a substantial portion of said ethanol passes down into said catalyst bed where a portion reacts with isobutene to form ethyl tertiary butyl ether, said ethanol and ethyl tertiary butyl ether being collected below said reaction distillation zone and above said first product stream as a second product stream and feeding said second product stream to said straight pass bed reactor.

If the ethanol contains water, the water is carried overhead with n-butenes, paraffins and other lights in the $C_4$ stream as a two phase azeotrope. The aqueous phase in the condensed overhead product is decanted and removed. The total liquid downflow from the reaction distillation zone is collected on a tray which may be perforated to allow upward passage of the vaporized components of the first product stream from the straight pass fixed bed reactor, which is substantially everything in the first product stream except the ETBE. The ETBE is removed and recovered.

When the second product stream is recovered from the column and returned as feed to the straight pass reactor, there is some inhibition of the ETBE reaction because of the presence of ETBE in the reactor inlet stream. However, the second product stream supplies the ethanol for the etherification in the straight pass reactor and dilutes the incoming $C_4$ feed thereby reducing the temperature from the exothermic etherification and reduces or eliminates other cooling that would be required without the dilution.

The straight pass reactor may have a fixed or fluidized bed.

DETAILED DESCRIPTION OF THE PREFERRED EMBODIMENTS

Figure 1:
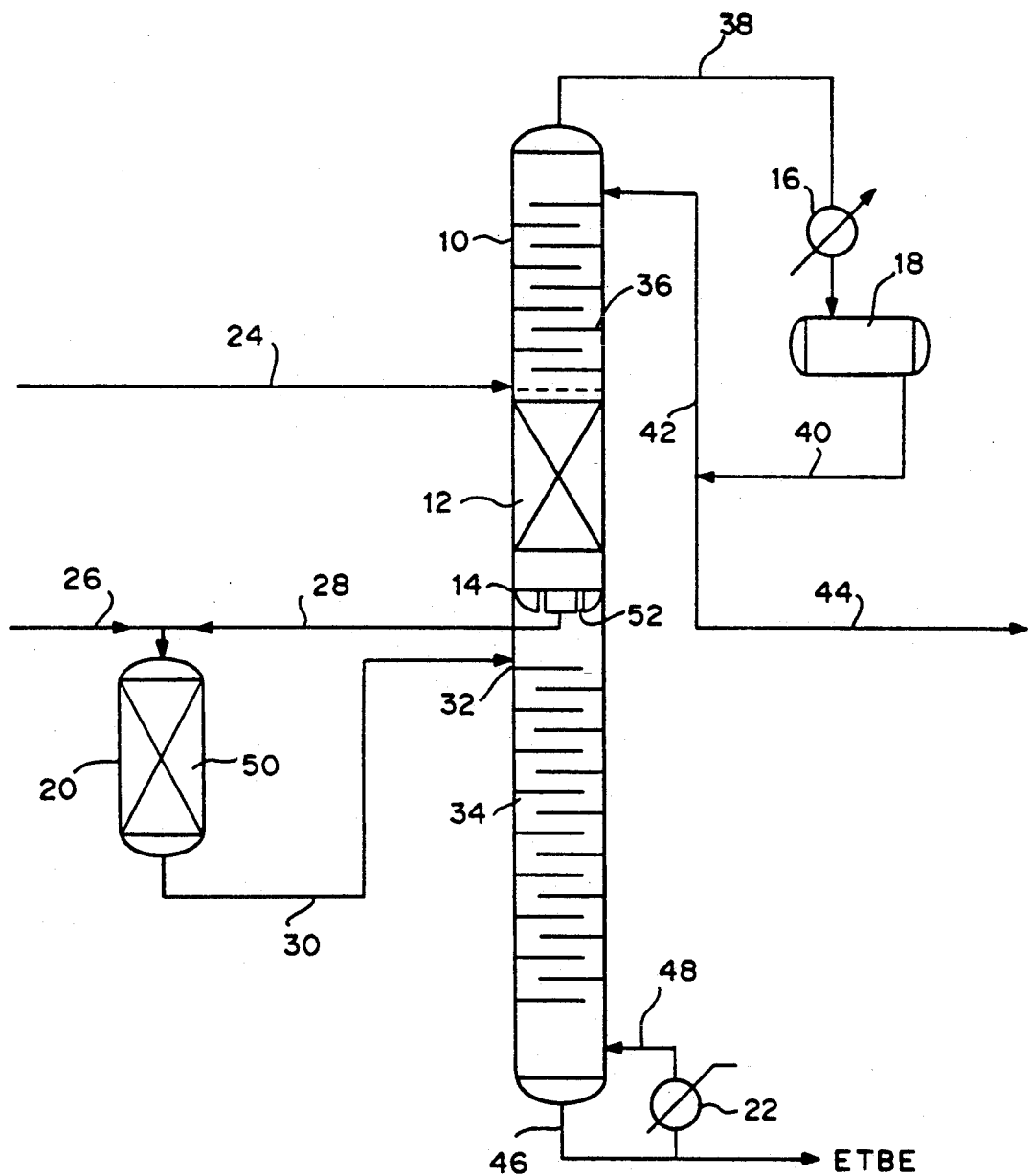
FIG. 1 is a flow diagram in schematic form of one embodiment of the present invention.

Mixed $C_4$ streams containing principally isobutane (I-$C_4$), normal butane (n-$C_4$), butene (B-1), isobutene (I-B), trans butene-2 (TB-2) and cis butene-2 (CB-2) (plus some minor impurities including butadiene). The $iC_4^=$ content of these streams is typically from 10–70 mole %, but may contain as little as 8 mole %.

The ethanol can be essentially water free or may contain up to 10 wt% water. The ethanol is fed to the system at generally a stoichiometric amount in relation to the isobutene present or in a slight excess. Substoichiometric ratios may also be used.

The temperature in the distillation column reactor is determined by the boiling point of the composition in the column at any given pressure, that is, at constant pressure a change in the temperature of the system, indicates a change in the composition in the column. Thus, to change the temperature the pressure is changed. By increasing the pressure, the temperature in the system in increased. Generally, pressures in the range of 0 to 400 psig are or may be employed, preferably 30 to 150 psig. For the $C_4$ stream, the present reaction will be carried out generally at pressures in the range of 10 to 300 psig, which will generally mean temperatures in the range of 10° to 100° C.

The reaction of isobutene with ethanol is equilibrium limited; however, by carrying out the reaction in a distillation column reactor and fractionating the formed product, ethyl tertiary butyl ether (ETBE), downward away from the reaction distillation zone, the equilibrium is constantly disrupted and hence the reaction never comes to equilibrium. This has the advantage of course, of achieving an effective 100% conversion, provided the catalyst bed is of sufficient length such that none of the isobutene escapes therefrom to go overhead with the n-butenes. The adjustment of the size of the catalyst bed is a mere mechanical step to be determined for each reactor and in accordance with the reaction conditions.

A reflux is preferably included in the system. The reflux ratio could vary over the rate of 0.5 to 20:1. In practice, the higher ratio may be used to compensate for a short catalyst bed such as required for experimental work. In commercial size units the catalyst bed would be provided so that lower reflux and hence higher unit productivity could be obtained.

A catalytic distillation process utilizes a distillation column reactor which contains one or more distillation zones and one or more reaction distillation zones. The zones are distinct because the distillation zones contain standard distillation structure such as inert packing or distillation trays. The reaction distillation zone contains a catalytic distillation structure which acts both as a catalyst for the reaction and a distillation structure for the fractional distillation of the mixture within the reaction distillation zone.

Catalysts suitable for the EtOH/$iC_4^=$ reaction to produce ETBE are cation exchange resins, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethyl benzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzene, divinyl toluene, divinylphenyl ether and others. The polymers may be prepared in the presence or absence or solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfuric acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C. and the sulfuric acid should contain sufficient sulfur trioxide after the reaction. The resulting products preferably contain an average of 1.3 to 1.8 sulfonic acid groups per aromatic nucleus. Particularly suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example German Patent Specification No. 908,247).

The ion exchange resin is preferably used in a granular size of about 0.25 to 1 mm, although particles from 0.15 mm up to about 1 mm may be employed. The finer catalyst particles provide high surface area, but also result in high pressure drops through the reactor. The macroreticular form of these catalysts is preferred because of the much larger surface area exposed and the limited swelling which all of these resins undergo in a non-aqueous hydrocarbon medium.

Similarly, other acid resins are suitable, such as perfluorosulfonic acid resins which are copolymers of sulfonyl fluorovinyl ethyl and fluorocarbon and described in greater detail in DuPont "Innovation", Volume 4, No. 3, Spring 1973 or the modified forms thereof as described in U.S. Pat. No.'s 3,784,399; 3,770,567 and 3,849,243.

In the preferred form the resin catalyst beads form too compact a bed and will not function adequately in a distillation, since there is a very large pressure drop through the bed and free flow of internal reflux and rising vapor is impeded. The resins may be used in the shape of conventional distillations structures, such as rings, saddles and the like. The particulate resins may be employed by enclosing them in a porous container such as cloth, screen wire or polymeric mesh. The material used to make the container must be inert to the reactants and conditions in the reaction system. The cloth may be any material which meets this requirement such as cotton, fiber glass, polyester, nylon and the like. The screen wire may be aluminum, steel, stainless steel and the like. The polymer mesh may be nylon, teflon or the like. The mesh or threads per inch of the material to make the container is such that the catalyst is retained therein and will not pass through the openings in the material. Particles of about 0.15 mm size or powders may be used and particles up to about ¼ inch diameter may be employed in the containers. Containers and systems for using the particulate catalyst are variously described in commonly owned U.S. Pat. Nos. 4,215,011; 4,302,356 and 4,443,559 which are hereby incorporated by reference.

Each container containing a solid catalytic material comprises a catalyst component. Each catalyst component is intimately associated with a spacing component which is comprised of at least 70 volume % open space up to about 95 volume % open space. This component may be rigid or resilient or a combination thereof. The combination of catalyst component and spacing component form the catalytic distillation structure. The total volume of open space for the catalytic distillation structure should be at least 10 volume % and preferably at least 20 volume up to about 65 volume %. Thus desirably the spacing component or material should comprise about 30 volume % of the catalytic distillation structure, preferably about 30 volume % to 70 volume %. Resilient materials are preferred. One suitable such material is open mesh knitted stainless wire, known generally as demister wire, or expanded aluminum. Other resilient components may be similar open mesh knitted polymeric filament of nylon, teflon or the like. Other material, e.g., reticulated polyurethane foam (rigid or resilient) may be formed in place or applied around the catalyst component. In the case of larger catalyst components such from about ¼ to ½ inch pellets, spheres, pills and the like each such larger component may be individually intimately associated with or surrounded by the spacing component as described above. It is not essential that the spacing component entirely cover the catalyst component. It is only necessary that the spacing component intimately associated with the catalyst component will act to space the various catalyst components away from one another as described above. Thus, the spacing component provides in effect a matrix of substantially open space in which the catalyst components are randomly but substantially evenly distributed.

A preferred catalytic distillation structure for use herein comprises placing the cation exchange resin particles into a plurality of pockets in a cloth belt, which is supported in the distillation column reactor by open mesh knitted stainless steel wire by twisting the two together in a helical form. This allows the requisite flows and prevents loss of catalyst. The cloth may be any material which is inert in the reaction. Fiber glass cloth or "Teflon" cloth are preferred.

A preferred primary reactor is a straight pass fixed bed reactor as described in U.S. Pat. No. 4,950,834. As described there a given composition, comprising the reaction mixture, will have a different boiling point at different pressures, hence the temperature in the reactor is controlled by adjusting the pressure to the desired temperature within the recited range. The boiling point of reaction mixture thus is the temperature of the reaction and the exothermic heat of reaction is dissipated by vaporization of the reaction mixture. The maximum temperature of any heated liquid composition will be the boiling point of the composition at a given pressure, with additional heat merely causing more boil up. The same principle operates in the present invention to control the temperature. There must be liquid present, however, to provide the boil up, otherwise the temperature in the reactor will continue to rise until the catalyst is damaged. In order to avoid exotherms which will vaporize all of the reaction mixture, it is necessary to limit the amount of isoolefin in the feed to the reactor to about 60 wt.% of the total feed.

The preferable catalyst bed in the straight pass reactor may be described as a fixed continuous bed, that is, the catalyst is loaded into the reactor in its particulate form to fill the reactor or reaction zone, although there may be one or more such continuous beds in a reactor, separated by spaces devoid of catalyst. The resin catalyst may be any of those described above. This packing may also be used in the straight pass reactor.

The distillation column reactor is preferably operated in the "froth mode" as disclosed in U.S. Pat. No. 5,120,403 which is incorporated herein. That is, the column was operated at near flooding conditions such that the column was filled with a frothing liquid caused by the rising vapors through a liquid level maintained in the column. This insures complete wetting of the catalyst while still allowing for fractional distillation. The column is not "flooded" in the conventional sense by vapor flow, but rather by a downward liquid flow restricter to maintain a desired differential pressure which is expressed as the height of the "flooded" section of the column.

Two embodiments are depicted in the attached figures in which like components are given like numerals for ease of reference. The figures are flow diagrams in schematic form and some conventional equipment as pumps, controllers, and control valves are not included as they would be obvious to those of ordinary skill in the art of distillation column design.

Referring to FIG. 1 the embodiment using a high purity ethanol. The cation resin prepared as distillation structures are in reaction distillation zone 12 of column 10. Collecting tray 14 is positioned below zone 12 to collect all of the liquid downflow which is then sent by 28 to the straight pass fixed bed reactor 20, where the resin catalyst 50 is loaded in a bed. This liquid downflow contains inert $C_4$ components, unreacted isobutene, ETBE product and ethanol, which mixes with the incoming $C_4$ feed 26 and serves as a diluent which helps control the temperature in the fixed bed and eliminates the need t recycle product from reactor 20 as a diluent.

Reactor 20 in addition to being the primary reactor where up to about 85% conversion of isobutene in the C$_4$ feed obtained is also a guard bed for the catalyst in the column 10. The product stream 30 from reactor 20 contains all of the product ETBE which is recovered in the system by fractionation of this stream in the conventional distillation section 34 of column 10. The unreacted isobutene, some ethanol, normal butenes, isobutane, normal butane and lights are vaporized and pass up the column through openings 52 in collecting tray 14 and into the reaction distillation zone 12 where substantially all of the remaining isobutene is selectively reacted with downflowing ethanol entering via 24. ETBE and ethanol are separated in zone 12 by distillation from the unreacted vaporous components rising from section 34.

Tray 14 allows vapors to rise from section 34 of the column. Alternatively, the openings 52 could be omitted from tray 14 and the vapor from section 34 could be piped around the tray to bottom of zone 12 (not shown).

The unreacted components in reaction distillation zone 12 continue through the conventional tray section 36 where som of the ethanol is azeotroped overhead. The overheads 38 ar condensed in condenser 16 and collected in accumulator 18. The accumulated distillate 40 is split with a reflux 42 returning to the top of column 10 and a distillate recovery of stream 44.

Figure 2:
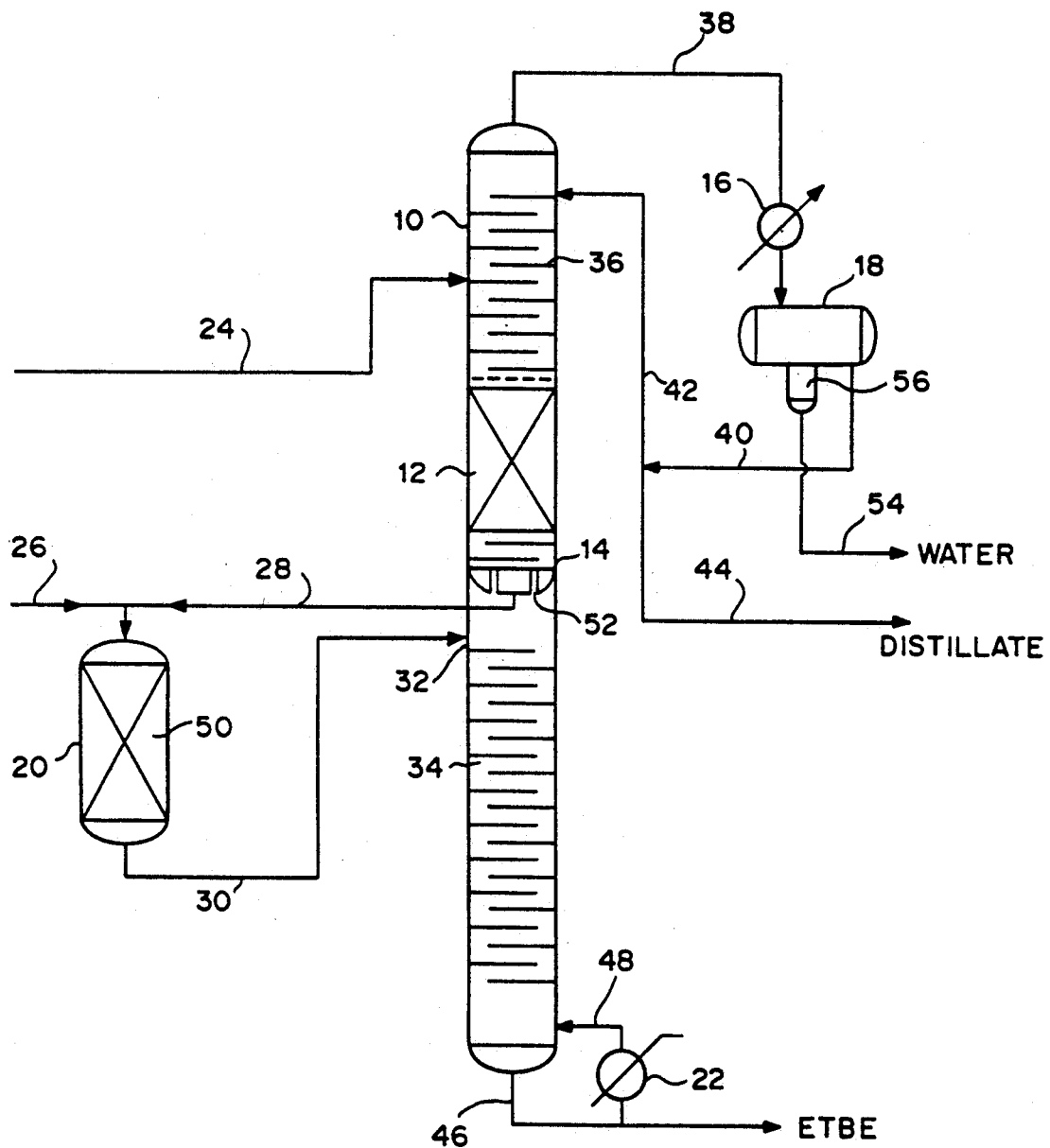
FIG. 2 is a flow diagram in schematic form of a second embodiment of the present invention, where 95% ethanol is used.

The process in FIG. 2 is the same as in FIG. 1 with only minor changes. The ethanol feed is 95 wt.% ethanol, 5 wt% water. The entry into the column 10 is desirably high in the conventional trays of section 36, to allow stripping of the water, which is carried overhead as part of the overheads 38, condensed at 16, and accumulated at 18. A boot 56 is provided to collect the water which is removed via 54.

The C$_4$-water azeotrope contains approximately 1 wt.% water, which is almost completely insoluble in the hydrocarbon. In most cases, there is enough hydrocarbon flow available in the distillation to carry the water contained in the EtOH feed, without the need to provide additional vapor. However, if necessary, the extra hydrocarbon vapor flow can be provided with a small increase in the column reflux ratio. Thus, by using the already-existing vapor and the C$_4$-water azeotrope, it is possible to remove the water from EtOH feed with little or no additional energy or equipment.

Most of the heat required for the distillation of the products is supplied through the reboiler 22, where a portion of the ETBE product 46 is vaporized and returned to the bottom of column 10 via line 48. The heat of reaction evolved in both the reaction distillation zone 12 and reactor 20 may be utilized in supplying sensible heat to the column feed 30 and as vapor for use in the reaction section 12 and the upper distillation section 36.

The invention claimed is:

1. A process for the production of ethyl tertiary butyl ether comprising feeding an isobutene-containing C$_4$ stream and a stream containing ethanol and ethyl tertiary butyl ether to a straight pass reactor containing an acid cation resin catalyst and selectively reacting ethanol and a portion of said isobutene to form a first product stream comprising ethanol, isobutene and ethyl tertiary butyl ether; collecting and feeding the total first product stream from said straight pass reactor to a catalytic distillation column reactor at a point below a reaction distillation zone and fractionating said first product stream to remove ethyl tertiary butyl ether as a bottoms product and vaporizing said ethanol and isobutene into said reaction distillation zone, feeding. ethanol to said column at a point above said reaction distillation zone wherein a substantial portion of said ethanol passes down into said reaction distillation zone; reacting a portion of said ethanol with isobutene to form ethyl tertiary butyl ether collecting said ethanol and ethyl tertiary butyl ether as a second product stream below said reaction distillation zone and above said first product stream and feeding said second product stream to said straight pass reactor with said C$_4$ stream.

2. The process according to claim 1 wherein said C$_4$ feed contains, normal butenes and butanes.

3. The process according to claim 2 wherein normal butenes and butanes are recovered as overheads.

4. The process according to claim 1 wherein said ethanol fed to said column above said reaction distillation zone contains water.

5. The process according to claim 4 wherein water is recovered as an overhead.

6. The process according to claim 2 wherein said ethanol fed to said column above said reaction distillation zone contains water.

7. The process according to claim 6 wherein water is recovered as an overhead azeotrope.

8. The process according to claim 1 wherein said C$_4$ stream contains 8-70 mole % isobutene.

9. A process for the production of ethyl tertiary butyl ether comprising the steps of:
(a) feeding a first stream containing isobutene to a downflow fixed bed reactor containing an acid cation exchange resin;
(b) feeding a second stream containing ethanol and ethyl tertiary butyl ether to said downflow fixed bed reactor;
(c) reacting a portion of said ethanol in said second stream with a portion of said isobutene in said first stream to form additional ethyl tertiary butyl ether;
(d) withdrawing a first product stream containing ethanol, ethyl tertiary butyl ether and isobutene from said downflow fixed bed reactor;
(e) feeding said first product stream to a distillation column reactor in a distillation zone below a reaction distillation zone wherein the ethyl tertiary butyl ether contained within said first product stream is separated from the ethanol and isobutene contained in said first product stream by fractional distillation, said ethyl tertiary butyl ether being removed as bottoms and said ethanol and said isobutene being boiled up into a reaction distillation zone;
(f) feeding a third stream containing ethanol to said distillation column reactor at a point above said reaction distillation zone;
(g) concurrently in said reaction distillation zone;
  (i) reacting the isobutene boiled up from said distillation zone with the ethanol boiled up from said distillation zone and the ethanol added in said third stream to form a reaction mixture containing ethyl tertiary butyl ether and unreacted ethanol;
  (ii) separating said ethyl tertiary butyl ether and said ethanol from any lighter components contained within said reaction mixture by fractional distillation;
(h) withdrawing said separated ethyl tertiary butyl ether and ethanol at a point below said reaction distillation zone as a second product stream;

(i) withdrawing said lighter components at a point above said reaction distillation zone as overheads; and (j) feeding said second product stream to said downflow fixed bed reactor.

10. The process according to claim 9 wherein said third stream contains water and said third stream is fed into a distillation zone above said reaction distillation zone wherein said water is separated from said ethanol and removed as overheads.

11. The process according to claim 9 wherein a portion of said overheads is condensed and returned to said distillation column reactor as reflux.

12. The process according to claim 11 wherein said third stream contains water and said third stream is fed into a distillation zone above said reaction distillation zone wherein said water is separated from said ethanol and removed as overheads and said water is separated from said condensed portion prior to returning said condensed portion as reflux.

13. The process according to claim 9 wherein the pressure of said downflow fixed bed reactor is adjusted such that the mixture within said reactor is boiling.

14. The process according to claim 9 wherein said first stream contains normal butenes and butanes.

15. The process according to claim 12 wherein said normal butenes and butanes are recovered as overheads.

16. The process according to claim 15 wherein said water is recovered as an azeotrope.

* * * * *